US010966875B2

(12) United States Patent
Heege et al.

(10) Patent No.: US 10,966,875 B2
(45) Date of Patent: Apr. 6, 2021

(54) APPARATUS AND METHOD FOR STRETCHING AND REPITCHING ELASTIC MEMBERS

(71) Applicant: ONTEX BVBA, Buggenhout (BE)

(72) Inventors: Thomas Heege, Duengenheim (DE); Michael Hochhausen, Münstermaifeld (DE)

(73) Assignee: ONTEX BV, Buggenhout (BE)

( * ) Notice: Subject to any disclaimer, the term of this patent is extended or adjusted under 35 U.S.C. 154(b) by 282 days.

(21) Appl. No.: 16/313,334

(22) PCT Filed: Jul. 20, 2017

(86) PCT No.: PCT/EP2017/068372
§ 371 (c)(1),
(2) Date: Dec. 26, 2018

(87) PCT Pub. No.: WO2018/024498
PCT Pub. Date: Feb. 8, 2018

(65) Prior Publication Data
US 2020/0179178 A1    Jun. 11, 2020

(30) Foreign Application Priority Data

Aug. 5, 2016 (EP) .................................... 16183096

(51) Int. Cl.
*A61F 13/15*  (2006.01)
*B29C 55/08*  (2006.01)
*B29L 31/48*  (2006.01)

(52) U.S. Cl.
CPC ........ *A61F 13/15601* (2013.01); *B29C 55/08* (2013.01); *B29C 55/085* (2013.01);
(Continued)

(58) Field of Classification Search
None
See application file for complete search history.

(56) References Cited

U.S. PATENT DOCUMENTS 5,407,507 A  4/1995  Ball
2012/0073729 A1* 3/2012 Giuliani .................. B29C 55/04
156/163

FOREIGN PATENT DOCUMENTS

EP  0236032 A2  9/1987
EP  2260813 A1  12/2010

OTHER PUBLICATIONS

European Search Opinion in European App. No. 16183096.3, dated Feb. 17, 2017.
(Continued)

*Primary Examiner* — Barbara J Musser
(74) *Attorney, Agent, or Firm* — Vivicar Law, PLLC

(57) ABSTRACT

The current invention concerns a method and apparatus for stretching and repitching an elastic member for attachment to a moving substrate, the elastic member being stretchable in at least a longitudinal direction and said elastic member in an essential non-stretched condition comprising an initial length along said longitudinal direction, the method comprising the steps of: (1) providing the elastic member in essentially non-stretched condition to a set of repitching members with an initial supply pitch, said set of repitching members comprising at least a first repitching member and a second repitching member, and optionally one or more repitching members arranged between said first and said second repitching member; (2) receiving said elastic members arranged in non-stretched condition between said set of repitching members, whereby the distance between the first and the second repitching member corresponds to the initial length of the elastic member; (3) moving at least said first and said second repitching members following trajectories diverging from each other, thereby stretching said elastic members arranged between the repitching members to an application length which is longer than the initial length and
(Continued)

which corresponds to the length of said elastic member in elastically stretched condition, whereby said repitching members are moved with selectively variable velocity when transferring said elastic members to selectively vary the application pitch of said elastic member in stretched condition on said substrate, the variation of the speed of said repitching members determining the application pitch of said elastic member in stretched condition on said substrate, characterized in that during step (3), said set of elastic members are rotated around a common rotation axis while the elastic member is being stretched from the initial length to the application length. Additionally, the invention concerns a method and apparatus for stretching and repitching an elastic member for attachment to a moving substrate whereby the elastic members are held by repitching members, which are rotated at an essentially constant rotational speed around rotation axes in trajectories, said trajectories being defined by having a different radial distance from the rotation axis to the repitching member rotating around said rotation axis at the application position where the elastic member is attached to the substrate, than at the initial position where the elastic member is received by the repitching members, thereby changing the pitch of the elastic members.

16 Claims, 8 Drawing Sheets

(52) U.S. Cl.
CPC .............. *B29C 2793/0081* (2013.01); *B29K 2995/0046* (2013.01); *B29L 2031/4878* (2013.01)

(56) References Cited

OTHER PUBLICATIONS

International Search Report and Written Opinion for PCT/EP2017/068372, dated Oct. 4, 2017.
Communication Pursuant to Article 94(3) EPC in European Application No. 16183096.3, dated Apr. 30, 2018.

* cited by examiner

Fig. 1 (PRIOR ART from EP2260813B1)

APPARATUS AND METHOD FOR STRETCHING AND REPITCHING ELASTIC MEMBERS

CROSS-REFERENCE TO RELATED APPLICATIONS

This application is the national stage application of corresponding international application number PCT/EP2017/068372, filed Jul. 20, 2017, which claims priority to and the benefit of European application no. 16183096.3, filed Aug. 5, 2016, all of which are hereby incorporated by reference in their entirety.

TECHNICAL FIELD

The invention pertains to the technical field of manufacturing a laminate comprising a substrate and one or more elastic members disposed on the substrate while being stretched. More particularly, the invention relates to a method and apparatus for stretching and repitching an elastic member for attachment to a moving substrate.

BACKGROUND

In the manufacturing of stretchable laminates, e.g. for use in hygienic disposables such as diapers, it is common to attach highly elastic members to substrates such as sheets which can be made of nonwoven material. Hereby, the substrates can have different elasticity properties than the elastic members, typically, the substrates have a smaller elasticity. In order for the laminate to be elastic, one option is to stretch the highly elastic member while it is attached to the substrate. As a result, once the attachment process is complete, the elastic member can be allowed to relax, thereby contracting the laminate, including the substrate, and offering the possibility e.g. to take on a certain 2D or 3D shape, or to be stretched during use, or to provide a better fit, etc.

One problem in manufacturing such laminates, i.e. laminates wherein an elastic member is stretched when it is attached to a substrate, is that the elastic members can be provided at a different pitch as the substrate. For instance, in a manufacturing process for diapers pants, an elastic member, e.g. an elastic strip, can be attached to a nonwoven sheet to ultimately form a stretchable front waist region. Herein, elastic strips are provided at a pitch P1, which typically can be the height of the strips, and which is related to the speed V1 of the strips according to $V1=P1 \times n1$, wherein n1 is the number of strips per unit of time. The nonwoven sheet can be provided in the form of an endless nonwoven at a speed V2, which can be cut later on in the process into individual articles at a rate of n2 articles per unit of time. Hence the pitch of the nonwoven is P2, whereby $V2=P2 \times n2$. In order to attach the strip to the nonwoven, the speed of both components need to be matched: $V1=V2$. If one strip needs to be attached per article, then $n1=n2$, and thus P1 needs to be the same as P2. If the initial value of P1 at which the strips are provided is lower than the initial value of P2 at which the nonwoven is provided, at least one of the two pitches needs to be altered. The present invention concerns a method and apparatus wherein the pitch P1 of the elastic members is adapted, typically increased, such that the speeds V1 of the elastic member and V2 of the substrate are matched during the actual attachment step. The term "repitching", within the context of this text, refers to this altering of the pitch of the elastic members.

European patent application EP 2 260 813 A1 discloses a device for forming elastication strips applicable in stretched condition (S'), for example along the waistline of sanitary articles (D) such as diapers and the like, the device including at least one pair of combined drawing members suitable for operating in gripping relation on the ends (A) of the strips to receive the strips themselves arranged bridge-like therebetween in non-stretched condition (S) at an inlet end (I) of the device, where said drawing members are at a first distance corresponding to the length of the strips (S) in non-stretched condition (S). The drawing members are moveable according to trajectories diverging from each other to draw the strips arranged bridge-like therebetween towards an outlet end (O) of the device, where the drawing members are at a second distance, greater than the first distance and corresponding to the length of the strips in elastically stretched condition (S). The drawing members are moved by motor means with selectively variable velocity (K) when transferring the strips between the inlet end (I) and the outlet end (O) to selectively vary the application pitch (P2) of the strips in stretched condition (S') on the sanitary articles (D). The drawing members operate on the ends of the strips (A) in a gripping relation without fastening or pinching, i.e. through vacuum pressure and/or hooking formations. This document thus discloses a method wherein repitching and stretching of an elastic strip is performed simultaneously.

However, the applicant has observed that the above disclosed method presents a number of disadvantages. One disadvantage is that the thusly formed laminate shows an uneven wrinkling at and around the region where the strip is applied, the uneven wrinkling leading to a distorted appearance of the final product and, more importantly, to a spread in the shape of many final products, leading to possible difficulties in subsequent packaging of a plurality of products and also to a set of products which are intended to be the same but do not look like they are the same.

There remains a need in the art for an improved method and apparatus for repitching and stretching elastic members for attachment to a moving substrate, which aims to resolve at least some of the problems mentioned above.

The invention thereto aims to provide a method and apparatus which ensures that the laminate and/or the final product comprising the laminate assumes the intended shape and/or an even contraction upon relaxation of the elastic member of the laminate.

SUMMARY OF THE INVENTION

The present invention provides a method and apparatus for stretching and repitching an elastic member for attachment to a moving substrate.

The methods and apparatuses according to the present invention allow even stretching of elastic members, in particular of elastic strips, while being repitched in order to be provided on a moving substrate.

According to a first aspect, the present invention concerns a method for stretching and repitching an elastic member for attachment to a moving substrate, the elastic member being stretchable in at least a longitudinal direction and said elastic member in an essential non-stretched condition comprising an initial length along said longitudinal direction. The method comprises the steps of:

(1) providing the elastic member in essentially non-stretched condition to a set of repitching members with an initial supply pitch, said set of repitching members comprising at least a first repitching member and a second repitching member, and optionally one or more repitching members arranged between said first and said second repitching member;

(2) receiving said elastic member arranged, preferably bridge-like, in non-stretched condition between said set of repitching members, whereby the distance between the first and the second repitching member corresponds to the initial length of the elastic member;

(3) moving at least said first and said second repitching members following trajectories diverging from each other, thereby stretching said elastic members arranged, preferably bridge-like, between the repitching members to an application length which is longer than the initial length and which corresponds to the length of said elastic member in elastically stretched condition, whereby said repitching members are moved with selectively variable velocity when transferring said elastic members to selectively vary the application pitch of said elastic member in stretched condition on said sheet, the variation of the speed of said repitching members determining the application pitch of said elastic member in stretched condition on said sheet, characterized in that during step (3), said set of elastic members are rotated around a common rotation axis while the elastic member is being stretched from the initial length to the application length.

In step (1) above, the elastic member, which preferably is an elastic strip, more preferably an essentially rectangular elastic strip, is provided with an initial supply pitch P1. It is provided to a set of repitching members, containing at least two members, in a non-stretched condition. The set of repitching members may comprise one or more additional members which can provide extra attachment and/or better controlled stretching during the repitching.

In step (2), the elastic members are received by the set of repitching members. The first and the second of the set of repitching members hereby receive a first end and a second end of the elastic member, respectively, and the distance between the first and the second of the set of repitching members corresponds to the initial length of the elastic member, i.e. in a non-stretched condition, such that the elastic member is engaged at least at or near its ends. If one or more additional repitching members are present between the first and second repitching members, these additional repitching members also receive the elastic member at a position between the first and second end of the elastic member.

In an embodiment, the steps (1) and (2) of providing the elastic member to the set of repitching members and or receiving the elastic member between the repitching members comprise supplying an elastic continuous web and cutting an elastic member, preferably an elastic strip, from said continuous web. Herein, preferably the repitching members are used as anvil for cutting the elastic member from the continuous web.

In step (3), the elastic member is being repitched and stretched in a simultaneous movement. Hereby, at least the first and said second repitching members follow trajectories diverging from each other and thereby stretch the elastic member which is arranged between the repitching members. The arrangement is preferably bridge-like, in the sense that at least part of the elastic member is not supported and thus spans a gap between the repitching members. The elastic member is stretched from an initial length in non-stretched condition to an application length, corresponding to the length which it can be applied to a moving substrate, typically by contacting the substrate and by bonding to the substrate, e.g. by gluing, welding, thermobonding, mechanical bonding, thermomechanical bonding, ultrasonic bonding, etc.

It is to be understood in step (3) that the set of elastic members being rotated around a common rotation axis signifies that the set of repitching members are rotated around the common rotation axis as well.

The resulting laminate can preferably be used or made in the manufacturing of hygienic disposables such as diapers, diaper pants, incontinence articles, etc., wherein upon relaxation of the elastic member, the laminate can be stretchable, feel soft, form a 3D shape, etc. Hence, the present invention also relates to methods of manufacturing hygienic disposables comprising the laminate as described in this document. In embodiments, the laminate is obtained and subsequently applied in the production of the hygienic disposables. In other embodiments, the laminate is obtained during the production of the hygienic disposables. In a particularly preferred embodiment, the method of manufacturing a hygienic disposable comprises the steps of:

stretching an elastic member, preferably an elastic strip;

applying the stretched elastic member to a first tensed continuous web or disposable pre-product, such as a diaper pre-product, according to a method and/or with an apparatus according to the present invention. Hereby, preferably the continuous web is held under tension, ensuring that the elastic member does not immediately relax;

optionally applying a second web material to the tensed continuous web, thereby sandwiching the elastic member in between the first and second web;

optionally cutting the continuous web or disposable pre-product comprising the elastic member, e.g. into separate diapers, and allowing the stretched elastic member to relax, thereby forming a wrinkled section in the laminate.

In order for the elastic member to be repitched, it is moved by the repitching members with selectively variable velocity when transferring the elastic member to selectively vary the application pitch P2 of the elastic member in stretched condition on the substrate, the variation of the speed of the repitching members determining the application pitch of said elastic member in stretched condition on said sheet.

In the present invention, the elastic member is being repitched by rotation of the set of elastic members around a common rotation axis. The elastic member is concurrently being stretched from the initial length to the application length by the repitching members which describe diverging trajectories. This latter is preferably achieved by increasing the distance between the first and second repitching members in the direction of the common rotation axis, e.g. by displacement of the first and/or the second repitching member during the rotation around the common axis.

Additionally, the invention provides a method for stretching and repitching an elastic member for attachment to a moving substrate, the elastic member being stretchable in at least a longitudinal direction and said elastic member in an essential non-stretched condition comprising an initial length along said longitudinal direction, the method comprising the steps of:

a. providing the elastic member in essentially non-stretched condition to a set of repitching members with an initial supply pitch, said set of repitching members comprising at least a first repitching member and a second repitching member, and optionally one or more repitching members arranged between said first and said second repitching member;

b. receiving said elastic members arranged in non-stretched condition between said set of repitching members, whereby the distance between the first and the second repitching member corresponds to the initial length of the elastic member;

c. moving at least said first and said second repitching members following trajectories diverging from each other, thereby stretching said elastic members arranged between the repitching members to an application length which is longer than the initial length and which corresponds to the length of said elastic member in elastically stretched condition;

whereby said repitching members are moved with selectively variable velocity when transferring said elastic members to selectively vary the application pitch of said elastic member in stretched condition on said substrate, the variation of the speed of said repitching members determining the application pitch of said elastic member in stretched condition on said substrate, whereby during step (3), the repitching members of the set each move in an essentially symmetric trajectory around a rotation axis, characterized in that the repitching members are moved in said trajectory at an essentially constant rotational speed, and whereby said trajectory is defined by having a different radial distance between the repitching members and the rotation axis in at least one point of the trajectory than the radial distance between the repitching members and the rotation axis at the point of the trajectory where the elastic members are provided to the repitching members.

Preferably, the repitching members are moved in said trajectory at an essentially constant rotational speed, and whereby said trajectory is defined by having a different radial distance between the rotation axis and a point of the trajectory where the elastic members are provided to the repitching members than between the rotation axis and at least one other point of the trajectory, thereby repitching the elastic members. More preferably, the trajectory is defined by having a different radial distance between the rotation axis and the point of the trajectory where the elastic members are provided to the repitching members than between the rotation axis and a point of the trajectory where the elastic members are applied to the substrate.

Preferably, said set of elastic members are rotated around a common rotation axis while the elastic member is being stretched from the initial length to the application length, preferably wherein said first and said second repitching members are rotated around the common rotation axis.

In EP2260813, the diverging trajectories of the first and second repitching members, therein termed 'drawing members', are embodied by the first drawing member being rotated around a first axis and the second drawing member being rotated around a second axis which is oblique with respect to the first axis. Such an embodiment indeed allows for simultaneous repitching and stretching of an elastic member. However, the induced stretch is uneven, which is particularly a problem for elastic strips wherein the amount of stretch at a front side of the strip is different from the amount of stretch on the back side of the strip, whereby the front-to-back direction of the strip basically refers to the direction in which the elastic strip is being repitched. Because of the use of a common rotation axis to rotate and repitch the repitching members and the elastic member arranged thereon, the problem of an uneven stretching of the elastic member is solved because the relative orientation of the repitching members remains the same during the repitching and stretching movement.

By ensuring an even stretching of the elastic members, the following effects are obtained:

the appearance of the laminate and the resulting wrinkled pattern is improved;

the amount of glue used in applying the evenly stretched members to a web is decreased. Hereby, one should note that in prior art methods wherein the elastic members were unevenly stretched, an unwanted 3D structure arose with spacings between surfaces to be glued. Hence more glue to fill out the spacings was required in prior art methods and apparatuses;

in case of heat-sealing bonding methods, the even stretching ensures a better bonding;

essentially no risk of enclosing foreign particles, e.g. fibers or SAP particles, between the elastic member and the substrate;

the eventual wrinkling of the relaxed laminate is generally obtained more efficiently, i.e. less material and/or less stretching of the elastic member is needed to create the same elastified section in the laminate due to the absence of unwanted 3D structure.

Furthermore, by increasing the distance between the first and second repitching members in the direction of the common rotation axis during rotation and repitching around said common axis, a better control of the repitching and stretching can be obtained, as the repitching profile and the stretching profile can be controlled at least partly independently. In EP2260813, the stretching profile and the repitching profile both depend on the rotational speed of the axes in a 1-on-1 relationship, i.e. in order to change the pitch from P1 to P2 (which depends on the laminating process characteristics) and to stretch the elastic strip from initial length to application length (the difference of which determines the angle of obliqueness between the two rotation axes), one only has control over the rotational speed profile which then determines both the profile of repitching and the profile of stretching. In the present invention, the repitching profile and the stretching profile can be controlled at least partly separately: the repitching profile can be determined by the rotational speed profile of the common rotation axis, while the stretching profile can also depend on the manner in which the distance between the first and second repitching members is increased during rotation. Hence, in a preferred embodiment of the present invention, the elastic member is repitched according to a predetermined repitching profile and the elastic member is stretched according to a predetermined stretching profile. Herein, the stretching profile preferably is defined as a function of the angular position of the elastic member, more preferably the stretching profile is an essentially sinusoidal function of the angular position. In an alternative preferred embodiment, the stretching profile is defined as a function of the time the elastic member has been arranged on the repitching members, more preferably the stretching profile comprises a portion which is an essentially linear function of the time the elastic member has been arranged on the repitching members.

The present invention also concerns an apparatus which is suitable for, and preferably arranged for, performing methods according to the present invention. The apparatus is hereby suitable for, and preferably arranged for, stretching and repitching an elastic member for attachment to a moving substrate. The apparatus hereby comprises:

a pivot axis defining a longitudinal direction;

a stretching device which is pivotably mounted on the pivot axis and capable of rotating around the pivot axis at least from an initial position to an application position, an actuator operatively coupled to the stretching device for rotating the stretching device around the pivot axis, said actuator suitable for, preferably configured for, repitching the elastic member from an initial pitch P1 at the initial position to an application pitch P2 at the application position;

a set of repitching members with at least a first repitching member and a second repitching member, and optionally one or more repitching members arranged between said first and said second repitching member, wherein at least said first and said second repitching members are displaceably mounted on said stretching device, such that the first and second repitching members can be displaced essentially along the longitudinal direction between an initial length and an application length;

a guiding device configured to define the displacement of at least the first and the second repitching members in correspondence with the stretching device, and preferably in correspondence with the position of the stretching device between said initial position and said application position.

Note that the terms 'initial length' and 'application length' can also be interpreted as 'initial distance' and 'application distance' between the repitching members as these will generally correspond to the length of the elastic members initially and upon application, or more exactly, the difference in initial and application length of the elastic members will be essentially equal to the difference in initial distance and application distance between the repitching members.

The apparatus allows the repitching members to stretch out the elastic member during rotation and thereby repitching the elastic member from P1 to P2 around the pivot axis.

Repitching can be arranged by configuring the actuator to rotate the stretching member around the pivot axis with a variable rotational speed, preferably such that that at the moment the elastic member is arranged on the repitching members at the initial position, the rotational speed of the stretching device corresponds with pitch P1 at which the elastic members are provided, whereby the rotational speed is subsequently altered such that the stretching device with the elastic member reaches the application position, the rotational speed corresponds to the application pitch P2 with which the elastic members need to be provided to the substrate.

In a preferred embodiment, the actuator comprises motor means with a selectively variable velocity for selectively varying the application pitch P2 of the elastic member in stretched condition on the moving substrate.

In order to stretch the elastic member, the repitching members of the apparatus can be configured to, during the repitching movement of the stretching device around the pivot axis, stretch the elastic member by increasing the distance between at least the first and the second repitching members, thereby increasing the elastic member's length from an initial length in a non-stretched condition to an application length in stretched condition. The manner in which the stretching is performed is arranged by the guiding device, which defines the displacement of the repitching members in a direction parallel to the pivot axis during the rotational movement of the stretching device.

In a preferred embodiment, the guiding device comprises at least one guiding rail, and preferably a pair of guiding rails. Each of the guiding rails is hereby positioned around the pivot axis and comprises a longitudinal inward-oriented guiding surface defining a path followed by at least the first repitching member or by at least the second repitching member.

In an aspect closely related to the above, the present invention also concerns a method for producing an elastified laminate with reduced uneven wrinkling, the laminate comprising a substrate and an elastic strip disposed thereon while being stretched, the elastic strip being stretchable in at least a longitudinal direction and said elastic strip in an essential non-stretched condition comprising an initial length along said longitudinal direction and a width along a transversal direction, comprising the steps of:

(i) providing an elastic strip in essentially non-stretched condition to a set of repitching members with an initial supply pitch, said set of repitching members comprising at least a first repitching member and a second repitching member, and optionally one or more repitching members arranged between said first and said second repitching member;

(ii) receiving said elastic strip arranged in non-stretched condition between said set of repitching members, whereby the distance between the first and the second repitching member corresponds to the initial length of the elastic strip;

(iii) moving at least said first and said second repitching members following trajectories diverging from each other, thereby stretching said elastic members arranged between the repitching members to an application length which is longer than the initial length and which corresponds to the length of said elastic strip in elastically stretched condition, whereby said repitching members are moved with selectively variable velocity when transferring said elastic strip to selectively vary the application pitch of said elastic strip in stretched condition on said substrate, the variation of the speed of said repitching members determining the application pitch of said elastic strip in stretched condition on said substrate;

(iv) attaching said elastic strip to the substrate at the application pitch, thereby obtaining an elastified laminate, characterized in that the elastic strip is stretched evenly across its width during said repitching step (iii), thereby reducing uneven wrinkling in the elastified laminate.

Further embodiments are described below and in the claims.

DETAILED DESCRIPTION OF THE INVENTION

Figure 1:
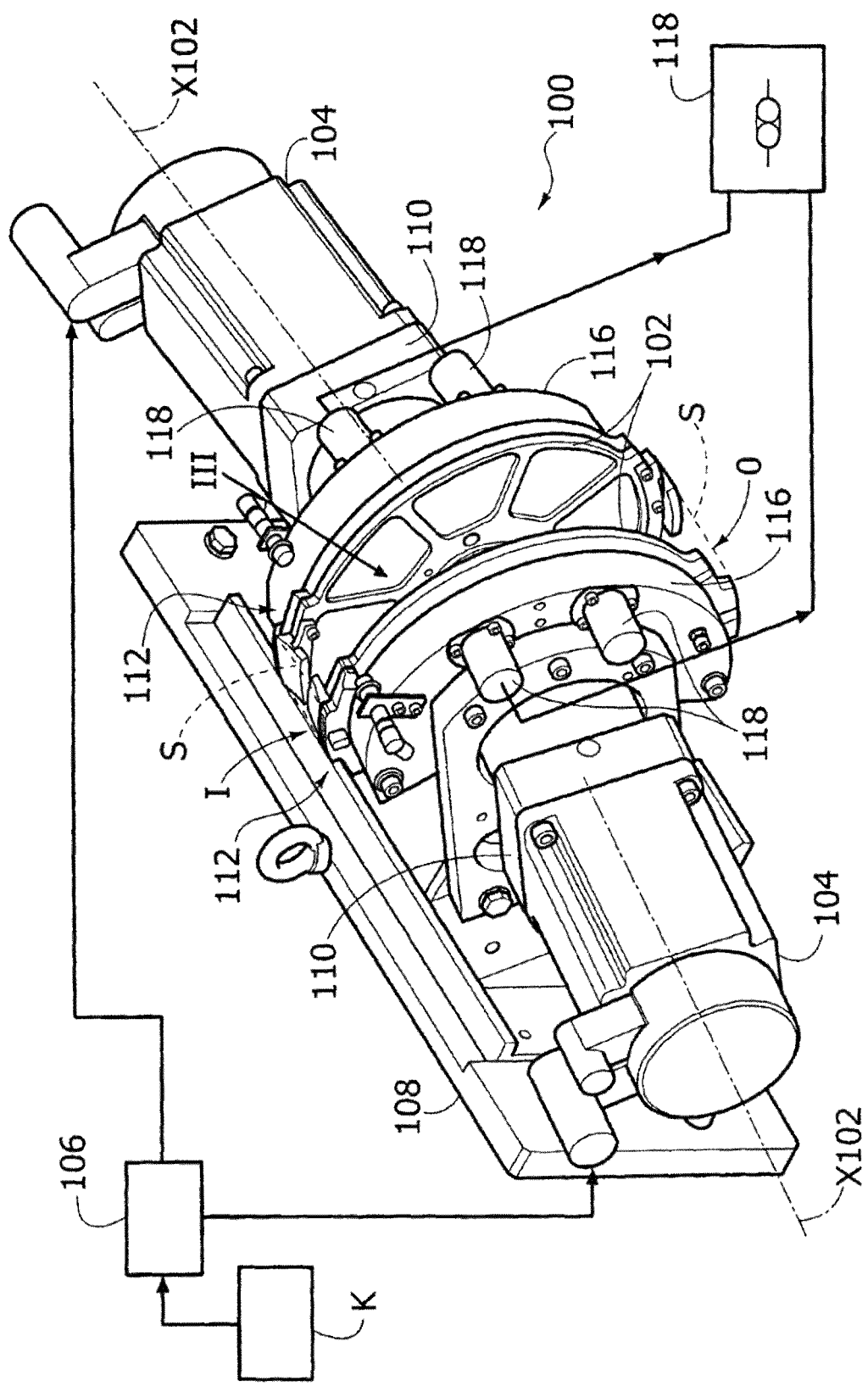
FIG. 1 illustrates an apparatus for repitching and stretching elastic strips from the prior art, in particular from EP2260813.

The present invention concerns methods and apparatuses for stretching and repitching an elastic member for attachment to a moving substrate, and preferably for even stretching of elastic members, in particular of elastic strips, while being repitched in order to be provided on a moving substrate.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The term "bridge-like" as referred herein with respect to the arrangement of the elastic members on or between the repitching members, refers to an arrangement whereby the elastic members are supported by the repitching members and are at least partially unsupported in between two adjacent elastic members, thereby spanning the gap between repitching members.

In an embodiment of the methods of the present invention, the elastic member is an elastic strip.

In an embodiment of the methods of the present invention, the elastic member is repitched according to a predetermined repitching profile, and the elastic member is stretched according to a predetermined stretching profile which is an essentially sinusoidal function of the angular position.

In an embodiment of the methods of the present invention, the elastic member is stretched according to a predetermined stretching profile, wherein the stretching profile comprises a portion which is an essentially linear function of the time the elastic member has been arranged on the repitching members.

In an embodiment of the methods of the present invention, the elastic member is arranged bridge-like between said set of repitching members when the elastic member is in non-stretched condition and/or is being stretched.

In an embodiment of the methods of the present invention, two, three, four or more sets of repitching members each comprise at least a first repitching member and a second repitching member, and optionally one or more repitching members arranged between said first and said second repitching member, whereby an elastic member is received by each set of repitching members as in step (2), and whereby each set of repitching members are moved as in step (3) to repitch and stretch each of the elastic members subsequently, simultaneously or partially simultaneously, whereby each set of repitching members is rotated around said common rotation axis, and whereby during step (3), said set of elastic members are rotated around a common rotation axis while the elastic member is being stretched from the initial length to the application length.

In an embodiment of the apparatus of the present invention, the guiding device comprises a guiding rail which determines the trajectory of at least one of the first or the second repitching member, and the stretching device comprises a stretching actuator and a stretching block to which said at least one of the first or the second repitching member is attached, the stretching actuator being configured to force said stretching block to said guiding rail such that said at least one of the first or the second repitching member follows the trajectory determined by the guiding rail.

In an embodiment of the apparatus of the present invention, the guiding device is a longitudinal guiding device configured to define the longitudinal displacement of at least the first and second repitching members, the apparatus furthermore comprising a radial guiding device configured to define a radial displacement of at least the first and the second repitching members in correspondence with the position of the stretching device between said initial position and said application position, whereby said first and said second repitching members can be displaced by the radial guiding device essentially along the radial direction between an initial radial distance of the first and second repitching members to the pivot axis and an application radial distance of the first and second repitching members to the pivot axis, characterized in that the application radial distance is different (higher or lower) from the initial radial distance.

Note that an additional advantage of this embodiment is that the rotational speed at which the repitching members are moved over the trajectories defined by the guiding devices, can be kept essentially constant, as the change of pitch can be exacted by the variable effective distance of the repitching members to the axis around which they are rotated. By having a constant rotational speed, the applicant prevents any problems from occurring with the motor or actuator which controls the movement of the repitching members over the trajectories, when moving at a variable rotational speed. The variable rotational speed used to be necessary to accomplish the change of pitch.

In a further embodiment of the apparatus of the present invention, the radial guiding device further determines the trajectory and radial distance of the first and second repitching members to the pivot axis, whereby the stretching device comprises a radial actuator, the radial stretching actuator being configured to force the first and second repitching members to follow the trajectory and the radial distance determined by the radial guiding device, preferably whereby the longitudinal guiding device and the radial guiding device comprise a pair of communal guiding rails which communal guiding rails determine the trajectory of the first and the second repitching members.

By providing a radial stretching actuator, it is ensured the repitching members follow the desired trajectory. Note that the term "guiding rail" should be broadly interpreted as a trajectory-defining means.

In an event further embodiment of the apparatus of the present invention, whereby the longitudinal guiding device and the radial guiding device comprise a pair of communal guiding rails which communal guiding rails determine the trajectory of the first and the second repitching members, and whereby the radial actuator is configured to force the first and second repitching members against the communal guiding rails by exerting a radially oriented force on the first and second repitching members, whereby said radially oriented force is either directed away from or to the pivot axis.

The radial stretching actuator may be adapted to force the repitching members against the guiding rail both outwardly from the rotation axis and inwardly towards the rotation axis, basically by pulling or pushing the repitching members. This can for instance be accomplished via spring means.

In an embodiment of the apparatus of the present invention, the repitching members each comprise gripping means, preferably said griping means comprising vacuum suction means, for holding the elastic member to the stretching device.

In an embodiment of the apparatus of the present invention, the stretching device comprises at least one additional repitching member longitudinally disposed between said first and second repitching members, preferably whereby said the additional repitching member is non-displaceably mounted on the stretching device such that its trajectory during use of the apparatus essentially is a circle perpendicular to the pivot axis.

In an embodiment of the apparatus of the present invention, the apparatus comprises two, three, four or more stretching devices, each pivotably mounted on the pivot axis and capable of subsequently, simultaneously or partially simultaneously rotating around the pivot axis at least from an initial position to an application position.

In an embodiment of the apparatus of the present invention, the apparatus is configured to perform any one of the methods of the present invention.

In a further aspect of the present invention, an apparatus is provided for stretching and repitching an elastic member for attachment to a moving substrate, comprising:
  a. a first and a second guiding device, each defining a trajectory;
  b. a set of repitching members with at least a first repitching member and a second repitching member, and optionally one or more repitching members arranged between said first and said second repitching member,
    wherein at least said first repitching member is mounted on the first guiding device and adapted to be rotatably displaceable around a first rotation axis, whereby said first repitching member is configured for following the trajectory defined by the first guiding device around said first rotation axis;
    and wherein at least said second repitching member is mounted on the second guiding device and adapted to be rotatably displaceable around a second rotation axis, whereby said second repitching member is configured for following the trajectory defined by the second guiding device around said second rotation axis;
  c. an actuator operatively coupled to the repitching members for rotating the repitching members around the first and/or second rotation axis, said actuator configured for rotating the repitching members at a constant rotational speed at least from an initial position on the trajectories to an application position on the trajectories;
  whereby the first and second guiding devices are adapted to distance said first and second repitching members at an initial length from each other on the initial position and at an application length from each other on the application position, whereby said application length is higher than said initial length;
  whereby the first and second guiding devices are adapted to provide the first and second repitching members at the initial position whereby said first and second repitching members are respectively distanced from the first and second rotation axis at an initial radial distance;
  and to provide the first and second repitching members at the application position whereby said first and second repitching members are respectively distanced from the first and second rotation axis at an application radial distance;
  characterized in that the trajectories are defined by having at least one point on the trajectories whereby said at least one point is distanced from the respective rotation axes of the trajectories at a radial distance different from the initial radial distance and/or from the application radial distance.

In a preferred embodiment of the apparatus, said application radial distance is different from the initial radial distance. In this embodiment, it can be understood that the at least one point distanced from the respective rotation axis of the trajectories at a radial distance different from the initial radial distance and/or from the application radial distance, can be considered as being at the application position (although, logically an intermediate position between the application and initial position with an intermediate radial distance would necessarily be present as well, thus still clearly fulfilling the requirements of the previous embodiment).

In a particular aspect, the application radial distance is higher than the initial radial distance. In a different aspect, the application radial distance is lower than the initial radial distance.

In specific embodiments, the guiding devices are shaped to define a trajectory having a projection on a plane perpendicular to their specific rotation axis, which projection is for instance ovate, pear-shaped, ellipsoid or an otherwise quasicircular shape. However, the projection may simply be circular as well, with the rotation axis not being in the center of the circle. In principle however, any projection in which the intersection point of the rotation axis of the repitching member has a larger distance at the application position than at the initial position for the repitching member, will suffice.

The apparatus as discussed with variable radial distances for the guiding devices holds many advantages. For instance, in a further aspect, it can be made possible to place the initial and/or application position at a desired point on the trajectory of the guiding device, thus allowing the ratio of the radial distances to be selected carefully (and thus the pitch) for each particular product.

Furthermore, it may be possible to change the pitch to an intermediate pitch between initial and application position for a further action which requires a third pitch (aside from the initial and application pitch). A guiding device which defines a trajectory with a variable radial distance allows the user to achieve different pitches at different points of the trajectory.

The applicant found many advantages to be present in this specific embodiment, as is clear from what is described. Additionally, it is to be considered that many adaptations of the former aspect of the invention may be applied to this further aspect as well.

FIG. 1 illustrates an apparatus for repitching and stretching elastic strips from the prior art, in particular from EP2260813. Herein, the elastic strips can be provided at the inlet (I) in a nonstretched condition (S), the ends of the strips being gripped by gripping formations (112) which thus serve a repitching members or drawing members. The gripping formations are mounted on two wheels or discs (102), each being mounted on a rotation axis (X102), the two rotation axis intersecting in a point in between the discs (102). The two discs are rotated by respective motors (104), driven by a control module (106), in turn operated under control of a control device K, e.g. a PLC, supervising the general operation of the system in which the apparatus (100) is inserted. The angle at which the rotation axis (X102) intersect, and thus the relative angle between the discs (102) and the amount of stretch to be applied to the elastic strips, is controlled by the brackets (110) onto which the discs are mounted and which are further mounted to a fixed plate (108). The elastic strip can be arranged on the gripping formations (112) by vacuum and by mechanical hooking or interference. Vacuum suction can be provided through a collector (116) and connection mouths in combination with a vacuum pump (118). With this apparatus, elastic strips can be provided at the inlet (I) in a non-stretched condition (S) at a pitch P1 and delivered out the outlet (O) in a stretched condition (S') at a pitch P2.

The present invention improves upon the methods and apparatuses of the prior art in a number of respects, as discussed previously, and as will be shown with the aid of FIGS. 2 to 5.

Figure 2:
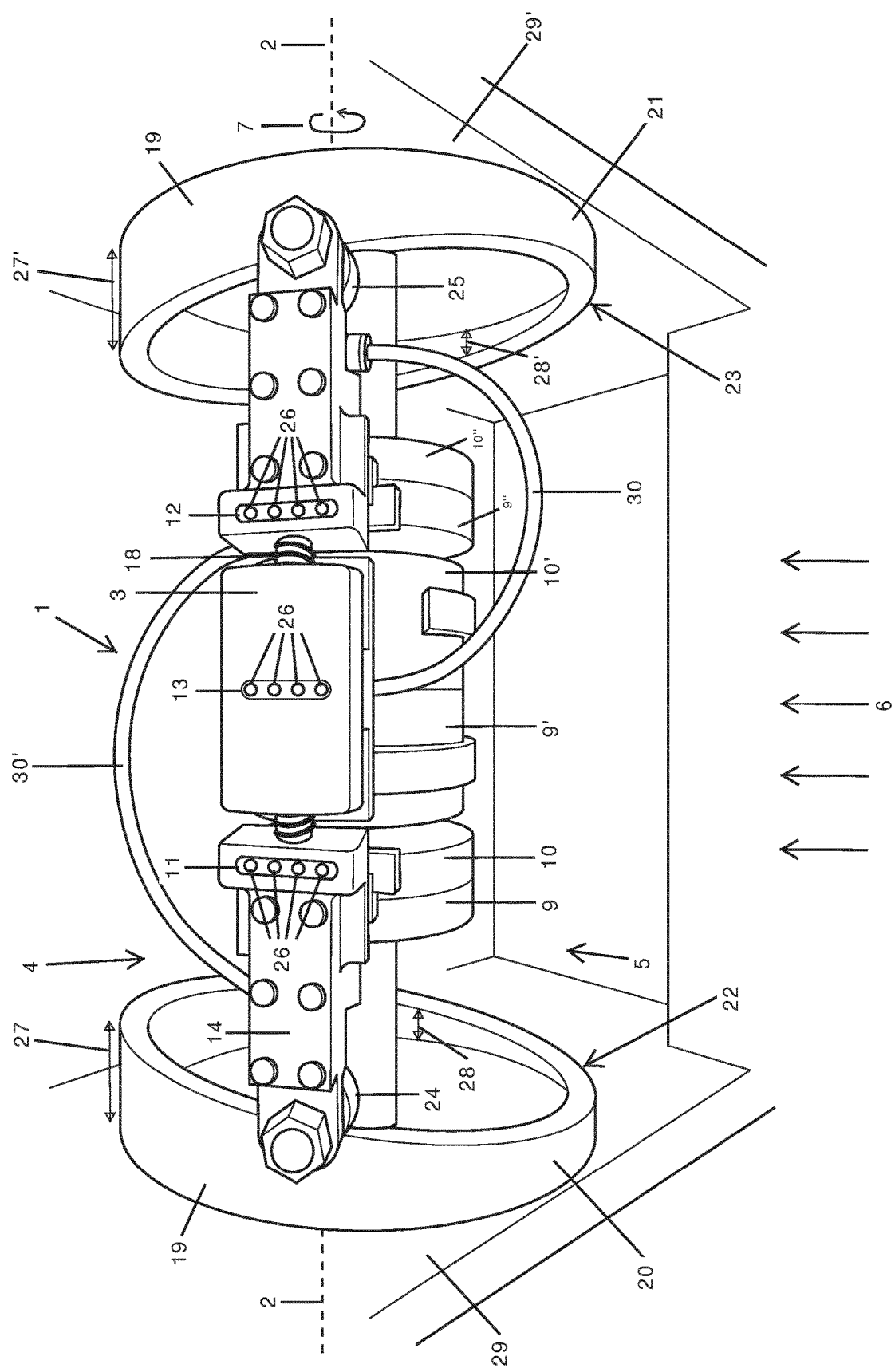
FIGS. 2 to 4 illustrate an embodiment of an apparatus according to the present invention, capable of performing the methods according to the present invention.
Figure 3:
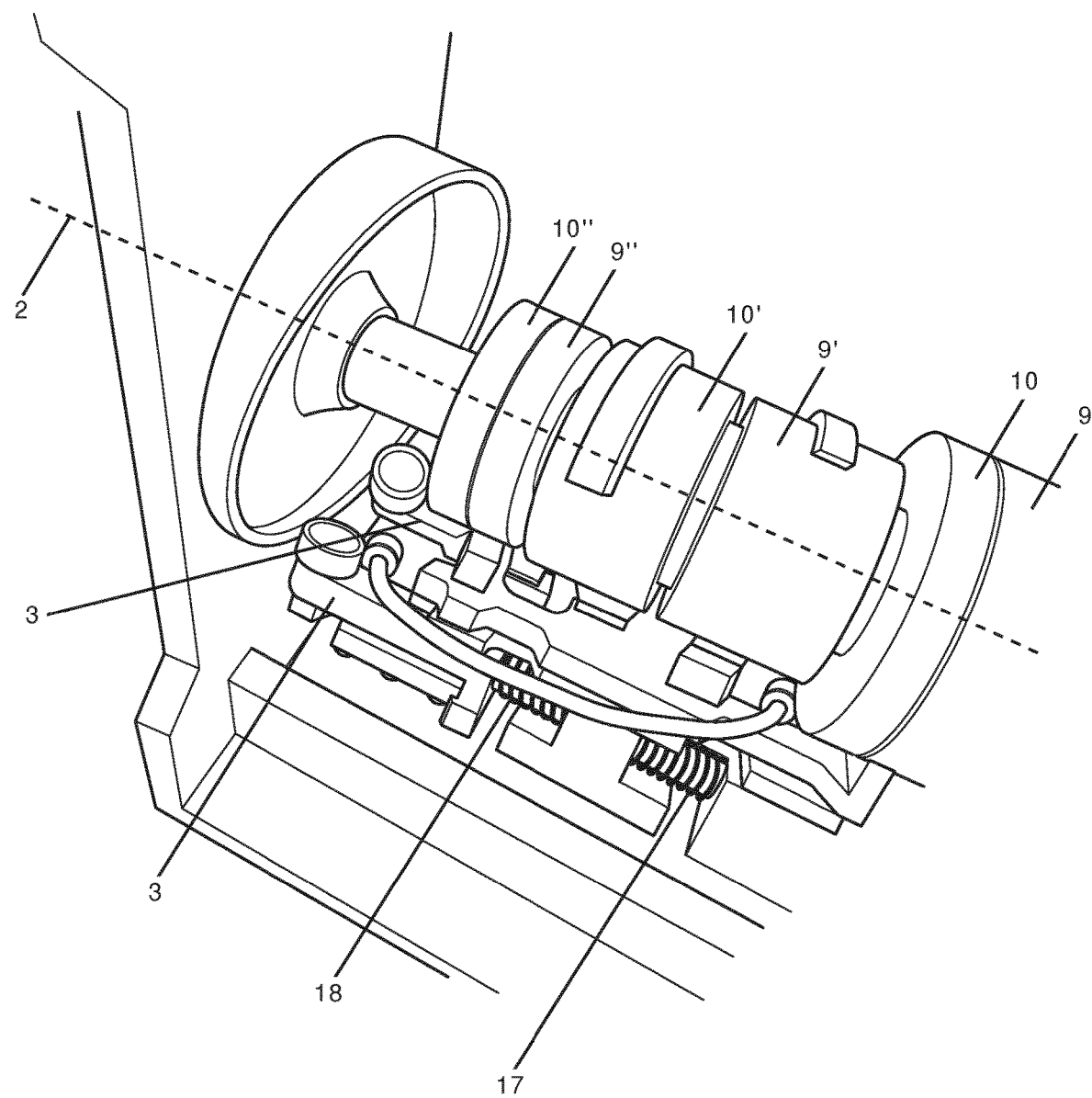
Figure 4:
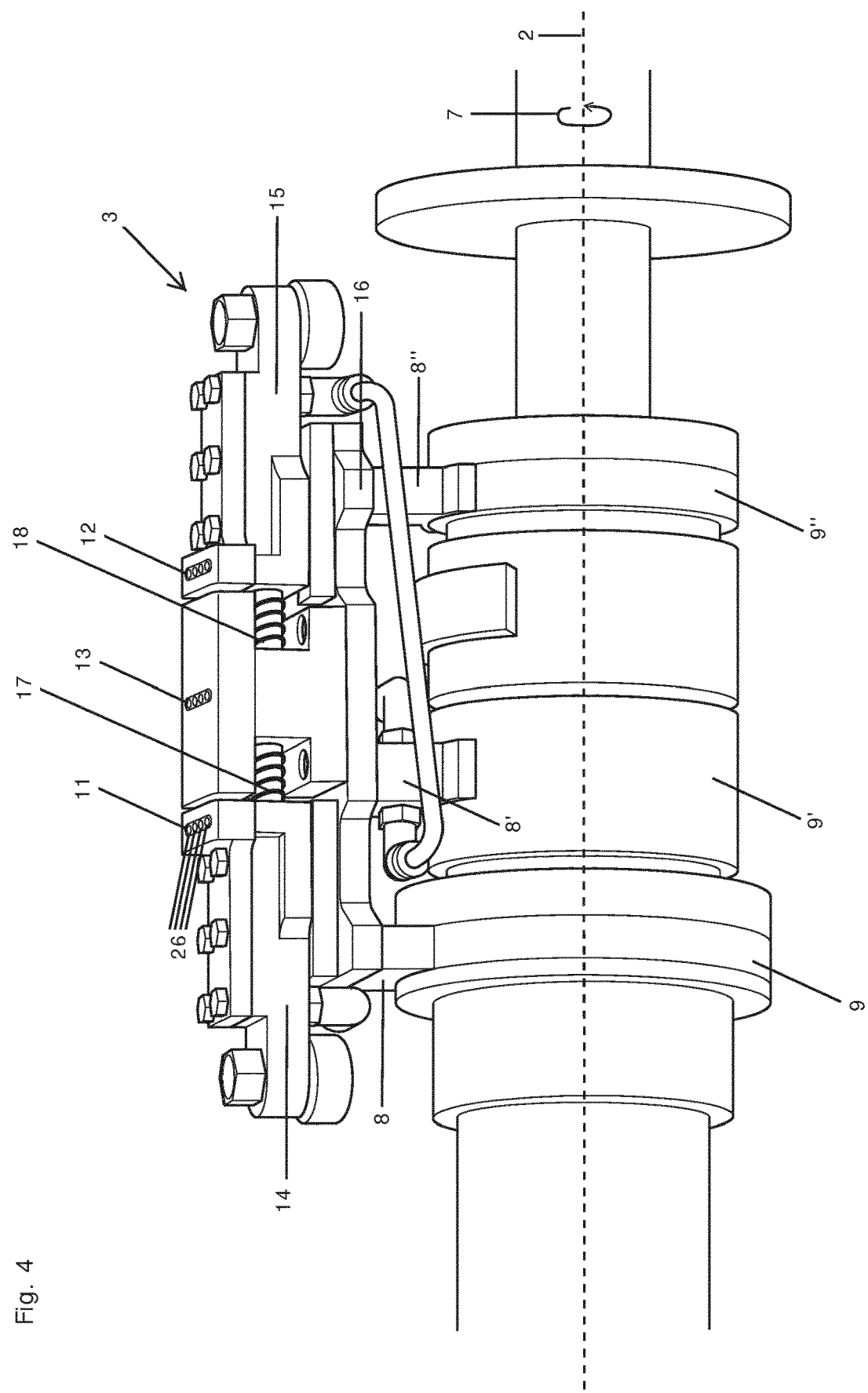

FIGS. 2 to 4 illustrate an embodiment of an apparatus of the present invention. The apparatus (1) comprises a pivot axis (2) defining a longitudinal direction. A stretching device (3) is pivotably mounted on the pivot axis and capable of rotating around the pivot axis at least from an initial position (4) to an application position (5) around the pivot axis (2) in the direction of the rotation arrow (7), whereby a substrate can be provided which moves in the direction of the arrows (6), i.e. such that the elastic member moves in the same direction an preferably at the same speed as the substrate at the application position (5).

An actuator is operatively coupled to the stretching device (3) by three connectors (8, 8', 8") which are attached to three respective wheels (9, 9', 9") which can be made to rotate around the pivot axis (2) by the actuator. As illustrated in FIG. 3, the apparatus may comprise a second stretching device (3'), which can be mounted with connectors on the pivot axis (2) via a second set of three wheels (10, 10', 10"). In further embodiments, the apparatus also comprises a third, fourth, fifth, sixth, . . . stretching device.

A set of repitching members (11, 12, 13) is mounted the stretching device (3). The set includes a first repitching member (11), a second repitching member (12) and one additional repitching member (13). The first (11) and second (12) repitching member engage with the respective ends of the elastic member. The distance between the first and second repitching member at the initial position (4) corresponds to the length of the elastic member in non-stretched condition, whereas the distance between the first and second repitching member at the application position (5) corresponds to the length of the elastic member in a stretched condition, ready to be applied to the substrate. The first (11) and second (12) repitching members are both displaceably mounted on the stretching device (3), by respective stretching blocks (14, 15) which can slide with respect to a stretching plate (16) of the stretching device (3) in a longitudinal direction.

In the embodiment illustrated in FIGS. 2-4, the stretching blocks (14, 15) with the first and second repitching members, are pushed longitudinally outwards by one or more stretching actuators, in the present embodiment being two respective springs (17, 18). Note that other stretching actuators than springs can also be used. More in particular, in an alternative embodiment, the stretching actuator can be a controlled extension device, e.g. one or more pneumatic or hydraulic actuators such as gas springs. The paths of the first and second repitching members are defined by the guiding device (19), which comprises a pair of guiding rails (20, 21), each comprising a longitudinally inwardly oriented surface (22, 23) describing a path around the pivot axis (2), the longitudinal position of which depends on the angle with the initial position (4). In the illustrated embodiment, the inwardly oriented surfaces essentially described a ring which can be created by cutting a cylindrical tube, which is centered around the pivot axis, along a straight plane at an oblique angle with the pivot axis, thereby creating a path whose longitudinal component is an essentially sinusoidal function of the angular position (or "azimuth", when using terminology from a cylindrical coordinate system). Hereby the distance (27, 27', 28, 28') of the inwardly oriented surface from a wall (29, 29') perpendicular to the pivot axis varies, whereby this distance at the initial position (27, 27') is larger than the distance at the application position (28, 28') in the figure. The stretching blocks each comprise a contact element, preferably a rotatably mounted wheel (24, 25), which is pushed by the corresponding stretching actuator against the corresponding longitudinally inwardly oriented surface (22, 23), such that the stretching block, and the repitching member mounted thereon, follows the path defined by the surface (24, 25) of the guiding means. Hence, in the shown embodiment, the stretching profile is an essentially sinusoidal function of the angular position of the stretching device. The path of one or both of the inwardly directed surfaces (22, 23) of the guiding rails (20, 21) can be altered such that other profiles can be obtained. In an alternative embodiment, the paths of the longitudinally inwardly oriented surfaces (22, 23) could be adapted such that the stretching profile comprises a portion which is an essentially linear function of the time the elastic member has been arranged on the repitching members, given a predefined repitching profile.

Each of the repitching members comprise gripping means for gripping the elastic member and keeping the elastic member attached to the repitching members during the repitching movement. In the shown embodiment, the repitching members comprise a number (e.g. 1, 2, 3, 4, 5 or more) of vacuum suction inlets (26), to which vacuum suction can be applied, e.g. through passages within the stretching blocks (14, 15) and tubings (30, 30') which are connected to a vacuum pumping system. The vacuum pumping system can be arranged to provide a vacuum during movement of the elastic member from the initial position (4) to the application position (5) and to stop providing the vacuum suction, and even to provide a blowing action, at the moment the elastic member reaches the application position (5).

Figure 5:
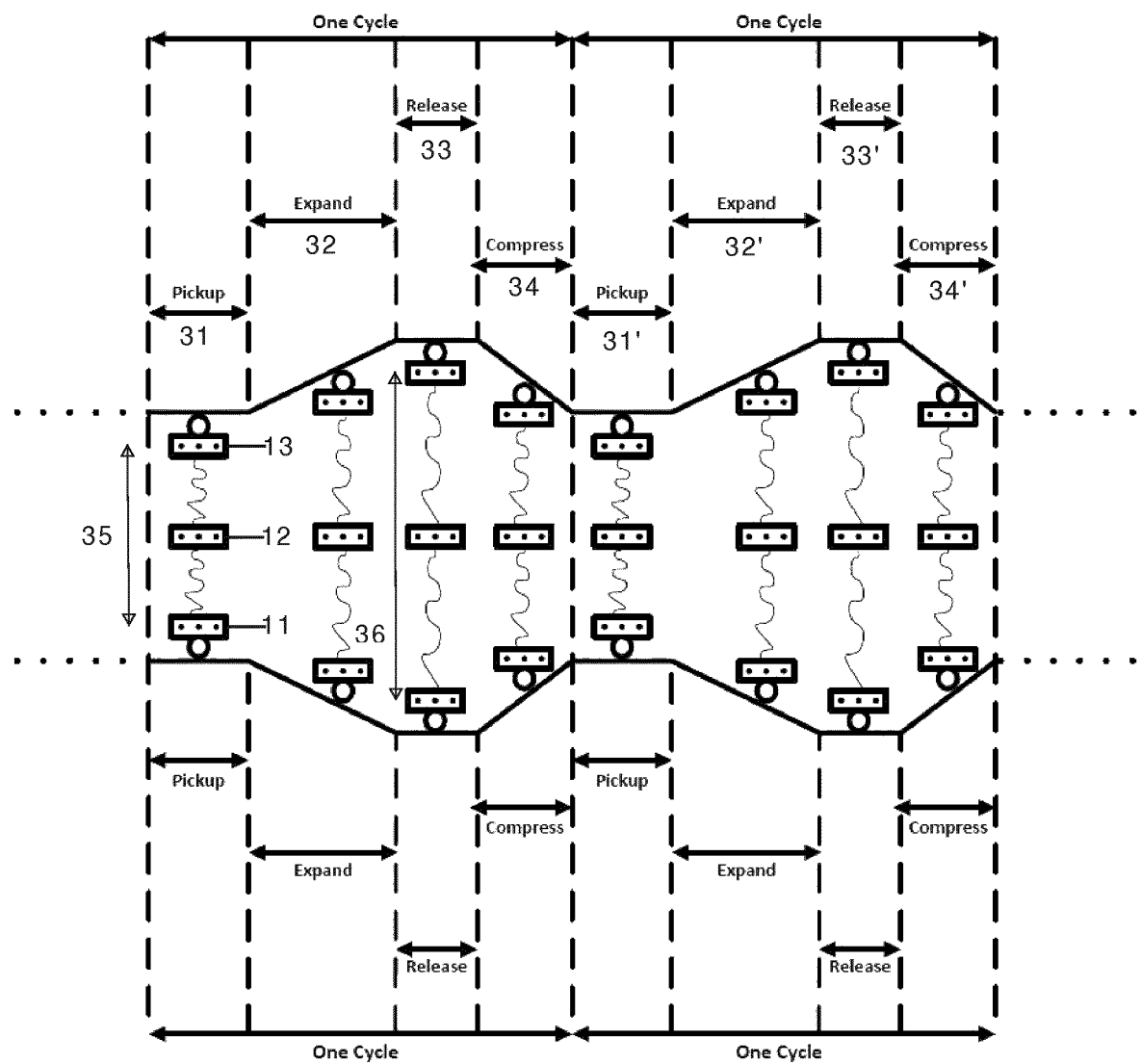
FIG. 5 illustrates a stretching profile and a repitching profile for elastic members according to the present invention.

An exemplary embodiment of a repitching profile and stretching profile is shown in FIG. 5. Herein, two consecutive cycles in time are shown. In a first phase (31, 31') of a cycle, an elastic member is being picked up by the repitching members. The first (11) and second (12) repitching members are at that moment separated by a distance (35) corresponding to the initial length of the elastic member in non-stretched condition. In a second phase (32, 32'), the distance between the first (11) and second (12) repitching members is increased, thereby stretching the elastic member. Note that the additional repitching member (13) does not change its longitudinal position in the shown embodiment, and thus describes a circular path around and perpendicular to the pivot axis. In a third phase (33, 33'), the elastic member has been stretched to its application length (36) and can be released from the repitching members in order to be applied to the moving substrate. In a fourth phase (34, 34'), the stretching device with the repitching members rotate further, or alternatively back to, the initial position while the distance between the first and second repitching members is compressed to the initial length of the next elastic member.

Figure 6:
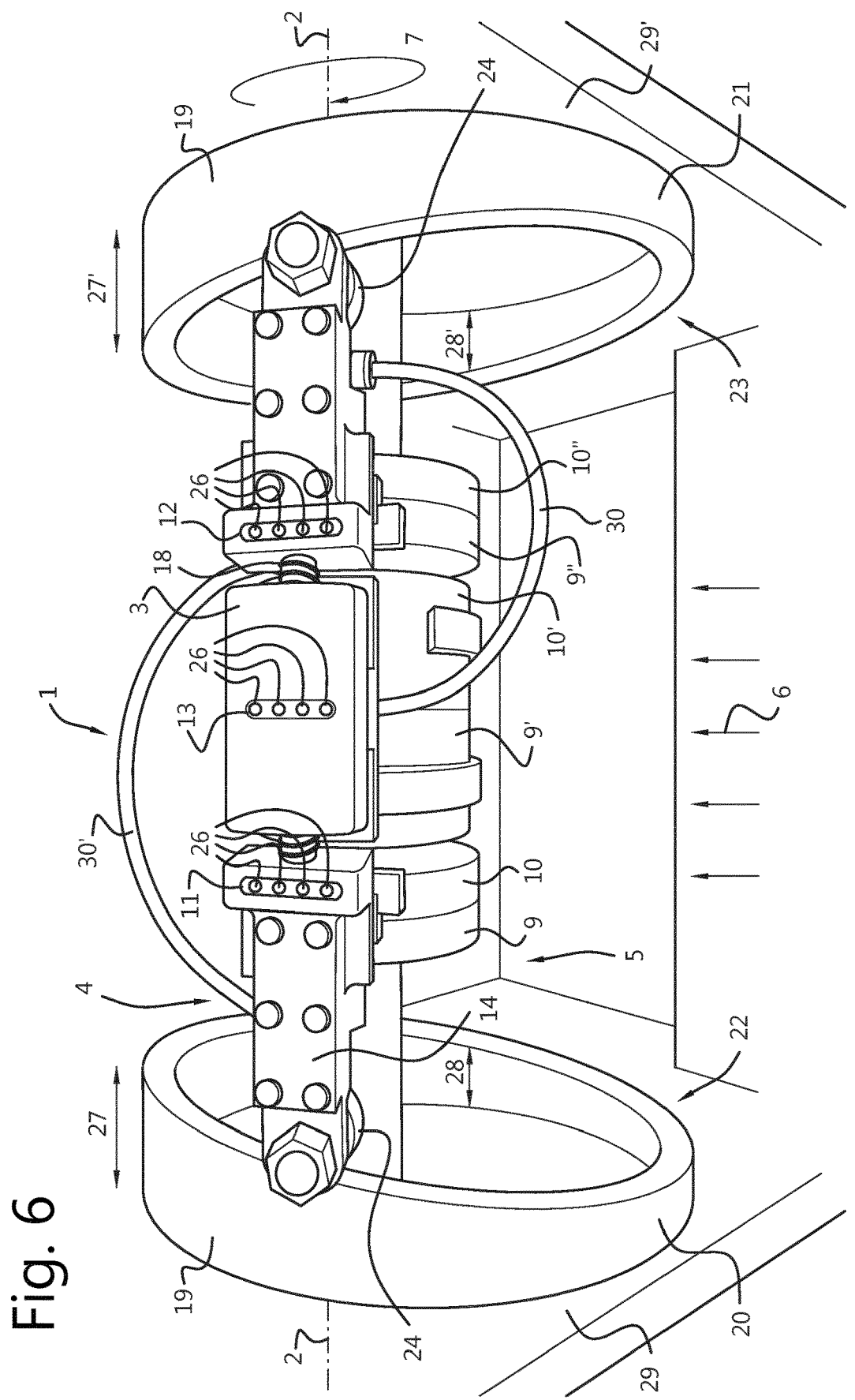
FIGS. 6 to 8 illustrate an alternative embodiment of an apparatus according to the present invention, capable of performing the methods according to the present invention, whereby the elastic members can be repitched under a constant rotational speed.
Figure 7:
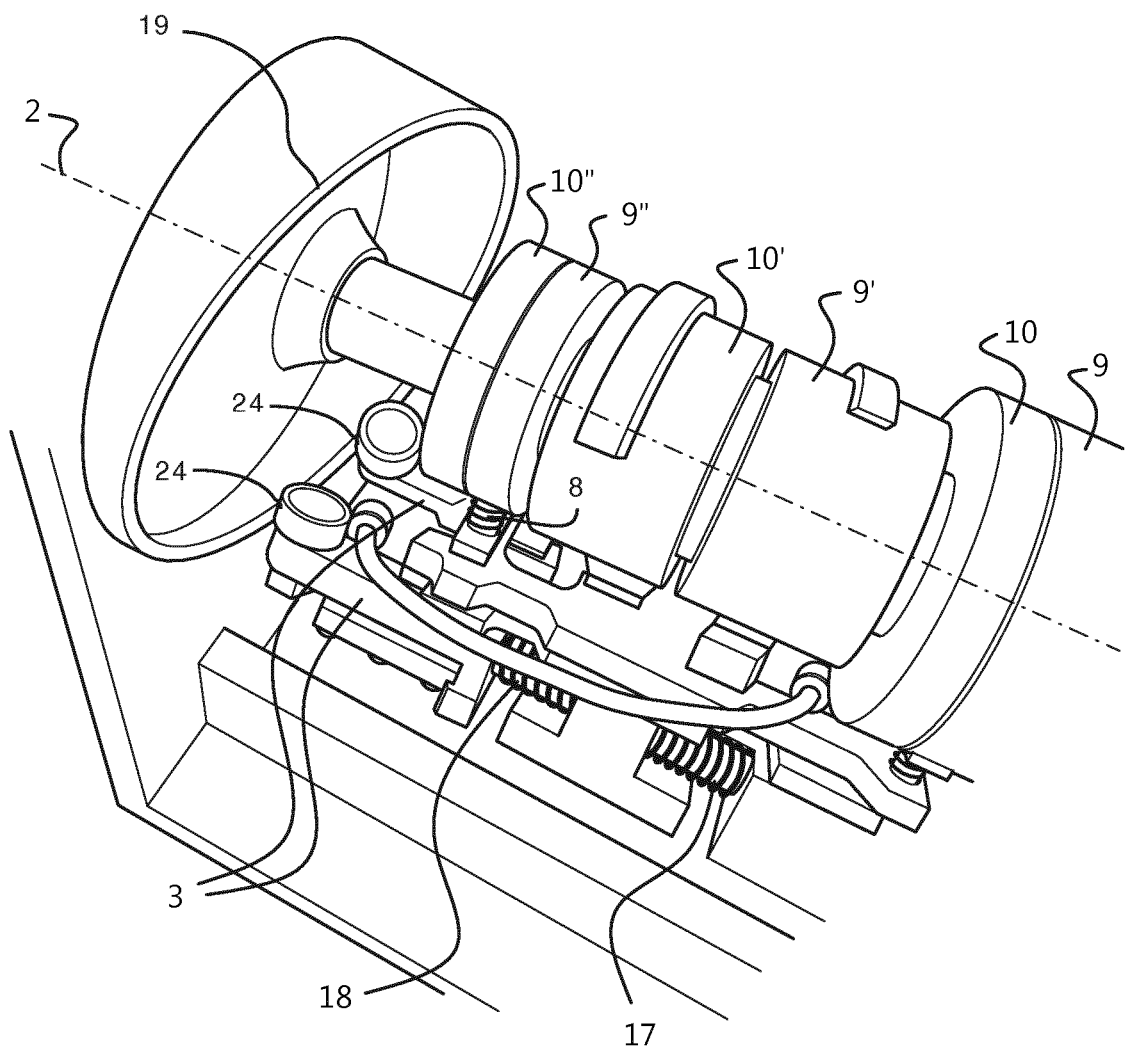
Figure 8:
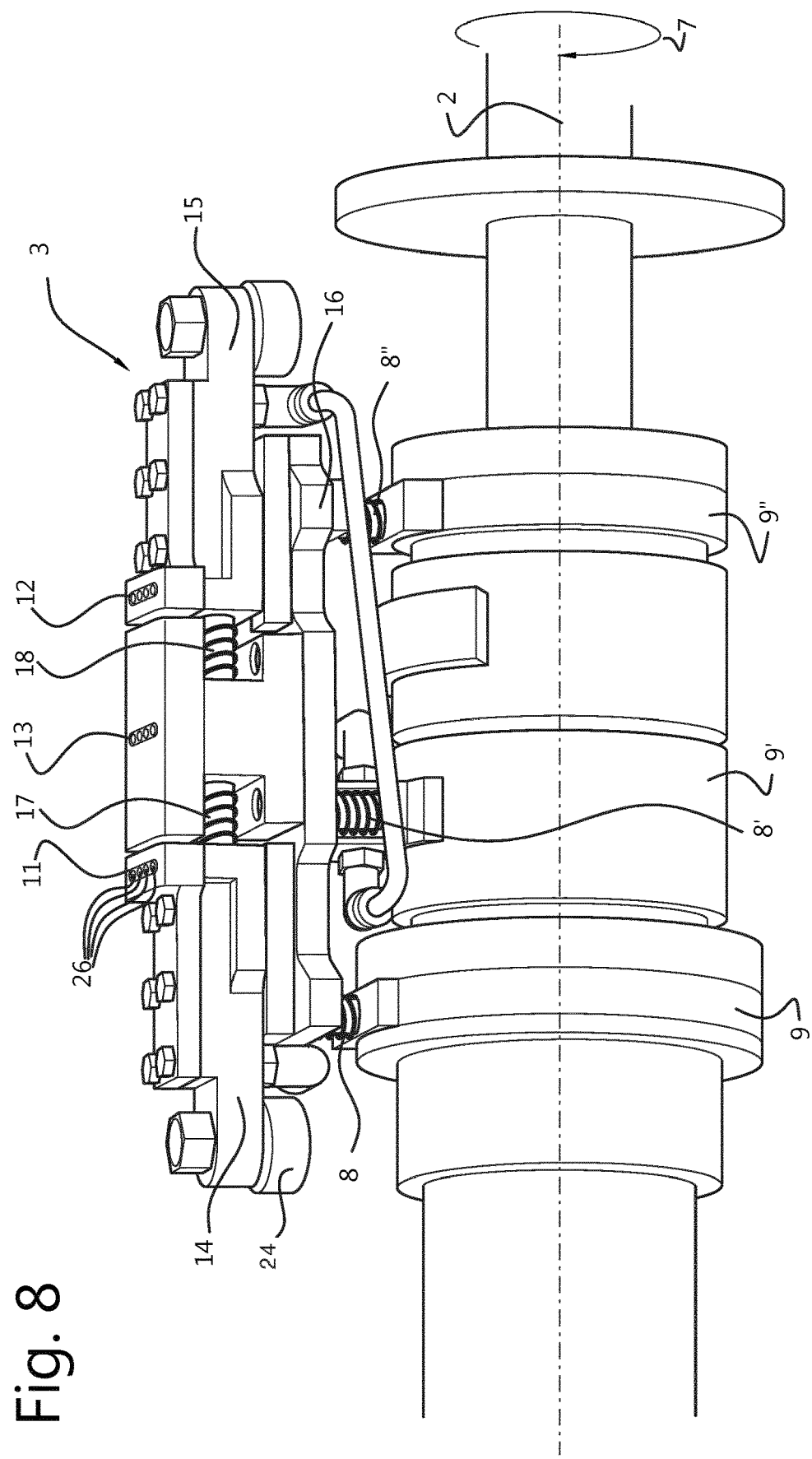

FIG. 6-8 show the invention in another aspect, wherein the apparatus is furthermore adapted to enable the repitching action without a specific repitching rotational speed profile. In the known embodiments, the repitching members rotate with a variable rotational speed, which is needed to allow the change of pitch. A variable rotational speed is much harder to set up, and to regulate, and requires a much more advanced actuator, which is taxed much harder by this variable regime. In these prior art forms, while the repitching members move from an initial position to an application position, the rotational speed is increased, thereby increasing the speed of the repitching members, and thus of the elastic members being held by the repitching members, which allows the elastic members to be provided at a large intervals from each other. The applicant cleverly avoids needing a set-up with a variable rotational speed by having the repitching members follow a non-circular trajectory under an essentially constant rotational speed. By requiring the distance of the repitching members to the axis around which the repitching members (and thus the elastic members) are rotated to be different at the application position than at the initial position, a different velocity is achieved at the application position, and a different pitch. Note that this distance can be higher at the application position, resulting in a higher velocity and a higher pitch, or lower. In a most preferred embodiment, the application and/or initial position can be shifted in order to obtain a particular ratio of radial distance, and thus achieving the desired pitch.

The applicant does not wish to be restricted to certain trajectories, and it is to be understood that any trajectory with variable distance of repitching members to the rotation axis (2), would suffice, if the apparatus is adapted to ensure the distance at the application position is different (higher or lower) from that at the initial position. Preferably however, the trajectory follows a continuous, fluent, smooth path, such as circular, ellipsoid, ovate, pear-shaped, or similar forms.

Note that the following example will largely describe a situation where the application radial distance is higher than the initial radial distance, but the opposite situation may easily be deduced from what follows.

The repitching members can be forced to follow this trajectory in a number of ways. One is to provide a physical radial guiding device which defines the trajectory, and upon which radial guiding device the repitching members are movably mounted, thereby ensuring that they follow the trajectory defined by the radial guiding device, while an actuator (typically mounted at the rotation axis) drives the repitching members to rotate with a constant rotational speed.

Alternatively, the radial guiding device may be an inhibiting guide, against which the repitching members are pushed (by an actuator), away from the rotation axis (2). Again, this ensures the repitching members to follow the defined trajectory, while it also allows easy control of the rotational speed of the repitching members. Inversely, the repitching members could be pulled to the rotation axis (2) and against the inhibiting guide.

FIG. 6 shows the guiding device (19) of the previous embodiment, adapted to allow the repitching of the elastic members at a constant rotational speed, by changing the trajectory defined by the guiding device (19). As one can see, the guiding devices (19) are adapted to have a longer distance between the rotation axis (2) around which the repitching members (11, 12, 13) are rotated, and the guiding device (19) itself, towards the bottom of the guiding device (19), where the elastic members are applied (repitched), when compared to the initial position towards the top of the guiding device (19). Considering the local speed at a rotational velocity of $\omega$ is $2\pi r\omega$, with r being the distance from the rotation axis (2), it is clear that the speed towards the bottom will be significantly higher than towards the top.

It is furthermore noteworthy that the proposed configuration could allow the easy replacement of the guiding devices (19) should a different pitch be desired at application, for instance when a different product is to be produced at a certain line. In prior art systems, this will necessitate reconfiguring the actuator and the speed profile, while now it merely requires replacing the guiding devices with ones that have the desired dimensions, thus reducing the problem of reconfiguring the actuators, calibrating and testing, to merely checking a simple mathematical formula for successfully picking the correct new guiding devices.

FIG. 7 additionally shows the set-up of the apparatus, in which a radial actuator (8) can be seen which can either push or pull the repitching members from or to the rotation axis (2). Preferably, the apparatus comprises one or more means adapted to interact with the radial guiding device (19) to ensure the repitching members (11, 12, 13) follow the trajectory defined by the radial guiding device (19). Such means are visible in FIG. 7, but can also be part of the contact element (24) in FIG. 6, and can be seen in FIG. 7 to inhibit further radial displacement once the contact element (24) is pressed against the radial guiding device (19).

FIG. 8 also shows springs (8, 8', 8") as an actuator (but also co-functioning as—part of—connectors) to ensure the repitching members are pressed (or pulled) against the guiding device (19) in the radial direction.

Note that the concept of providing trajectories with variable radial distances from repitching members to rotation axis (2) (with higher distance at application position than at initial position) can similarly be applied to different methods and apparatuses in which the repitching members are rotated around separate rotation axes, and should not be restricted.

The invention claimed is:

1. Method for stretching and repitching an elastic member for attachment to a moving substrate, the elastic member being stretchable in at least a longitudinal direction and said elastic member in an essential non-stretched condition comprising an initial length along said longitudinal direction, the method comprising the steps of:
   (1) providing the elastic member in essentially non-stretched condition to a set of repitching members with an initial supply pitch, said set of repitching members comprising at least a first repitching member and a second repitching member;
   (2) receiving said elastic members arranged in non-stretched condition between said set of repitching members, whereby the distance between the first and the second repitching member corresponds to the initial length of the elastic member;
   (3) moving at least said first and said second repitching members following trajectories diverging from each other, thereby stretching said elastic members arranged between the repitching members to an application length which is longer than the initial length and which corresponds to the length of said elastic member in elastically stretched condition, whereby said repitching members are moved with selectively variable velocity when transferring said elastic members to selectively vary the application pitch of said elastic member in stretched condition on said substrate, the variation of the speed of said repitching members determining the application pitch of said elastic member in stretched condition on said substrate, characterized in that during step (3), said set of repitching members are rotated around a common rotation axis while the elastic member is being stretched from the initial length to the application length.

2. Method according to claim 1, wherein the elastic member is an elastic strip.

3. Method according to claim 1, wherein the elastic member is repitched according to a predetermined repitching profile, and wherein the elastic member is stretched according to a predetermined stretching profile which is an essentially sinusoidal function of the angular position.

4. Method according to claim 1, wherein the elastic member is arranged bridge-like between said set of repitching members when the elastic member is in non-stretched condition and/or is being stretched.

5. Method according to claim 1, wherein two, three, four or more sets of repitching members each comprise at least a first repitching member and a second repitching member, whereby an elastic member is received by each set of repitching members as in step (2), and whereby each set of repitching members are moved as in step (3) to repitch and stretch each of the elastic members subsequently, simultaneously or partially simultaneously, whereby each set of repitching members is rotated around said common rotation axis.

6. A method for producing an elastified laminate with reduced uneven wrinkling, the laminate comprising a substrate and an elastic strip disposed thereon while being stretched, the elastic strip being stretchable in at least a longitudinal direction and said elastic strip in an essential non-stretched condition comprising an initial length along said longitudinal direction and a width along a transversal direction, whereby the elastic strip is an elastic member, whereby the elastic member is stretched and repitched for attachment to the moving substrate according to claim 1, further comprising the subsequent step of:

(iv) attaching said elastic member to the substrate at the application pitch, thereby obtaining an elastified laminate; characterized in that the elastic strip is stretched evenly across its width during said repitching step (iii).

7. Method according to claim 1, wherein the elastic member is stretched according to a predetermined stretching profile, wherein the stretching profile comprises a portion which is an essentially linear function of the time the elastic member has been arranged on the repitching members.

8. Method according to claim 5, wherein one or more repitching members are arranged between said first and said second repitching member.

9. Method according to claim 1, wherein one or more repitching members are arranged between said first and said second repitching member.

10. Apparatus for stretching and repitching an elastic member for attachment to a moving substrate, comprising:
a pivot axis defining a longitudinal direction;
a stretching device which is pivotably mounted on the pivot axis and capable of rotating around the pivot axis at least from an initial position to an application position,
an actuator operatively coupled to the stretching device for rotating the stretching device around the pivot axis, said actuator configured for repitching the elastic member from an initial pitch P1 at the initial position to an application pitch P2 at the application position;
a set of repitching members with at least a first repitching member and a second repitching member,
wherein at least said first and said second repitching members are displaceably mounted on said stretching device, such that the first and second repitching members can be displaced essentially along the longitudinal direction between an initial length and an application length;
a guiding device configured to define the displacement of at least the first and the second repitching members in correspondence with the position of the stretching device between said initial position and said application position.

11. Apparatus according to claim 10, wherein the guiding device comprises a guiding rail which determines the trajectory of at least one of the first or the second repitching member, and wherein the stretching device comprises a stretching actuator and a stretching block to which said at least one of the first or the second repitching member is attached, the stretching actuator being configured to force said stretching block to said guiding rail such that said at least one of the first or the second repitching member follows the trajectory determined by the guiding rail.

12. Apparatus according to claim 10, whereby the repitching members each comprise gripping means, said gripping means comprising vacuum suction means, for holding the elastic member to the stretching device.

13. Apparatus according to claim 10, whereby the stretching device comprises at least one additional repitching member longitudinally disposed between said first and second repitching members.

14. Apparatus according to claim 13, whereby said the additional repitching member is non-displaceably mounted on the stretching device such that its trajectory during use of the apparatus essentially is a circle perpendicular to the pivot axis.

15. Apparatus according to claim 10, comprising two, three, four or more stretching devices, each pivotably mounted on the pivot axis and capable of subsequently, simultaneously or partially simultaneously rotating around the pivot axis at least from an initial position to an application position.

16. Apparatus according to claim 10, wherein one or more repitching members are arranged between said first and said second repitching member.

* * * * *